United States Patent
van Lengerich et al.

(10) Patent No.: US 6,436,453 B1
(45) Date of Patent: *Aug. 20, 2002

(54) PRODUCTION OF OIL ENCAPSULATED MINERALS AND VITAMINS IN A GLASSY MATRIX

(75) Inventors: Bernhard H. van Lengerich, Plymouth; Jamileh Lakkis, Minneapolis, both of MN (US)

(73) Assignee: General Mills, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/595,121

(22) Filed: Jun. 16, 2000

(51) Int. Cl.[7] .......................... A23L 1/302; A23L 1/303; A23L 1/304; A23L 1/09

(52) U.S. Cl. ............................. 426/74; 426/72; 426/73; 426/97; 426/98; 426/99; 426/103; 426/516; 426/518

(58) Field of Search ............................. 426/72, 73, 74, 426/97, 98, 99, 103, 516, 518

(56) References Cited

U.S. PATENT DOCUMENTS

| | | |
|---|---|---|
| 2,876,160 A | 3/1959 | Schoch et al. |
| 3,027,102 A | 3/1962 | Lödige et al. |
| 3,404,984 A | 10/1968 | Olsen |

(List continued on next page.)

FOREIGN PATENT DOCUMENTS

| | | |
|---|---|---|
| DE | 40 21 678 | 1/1992 |
| EP | 336662 A | 10/1989 |
| EP | 391518 A | 10/1990 |

(List continued on next page.)

OTHER PUBLICATIONS

Per Artusson et al., "Characterization of Polyacryl Starch Microparticles as Carriers for Proteins and Drugs," *Journal of Pharmaceutical Science*, vol. 73, No. 11, pp. 1507–1513 (Nov. 1984).

(List continued on next page.)

*Primary Examiner*—Helen Pratt
(74) *Attorney, Agent, or Firm*—John A. O'Toole; Douglas J. Taylor; Barry I. Hollander

(57) ABSTRACT

A mineral or vitamin fortification ingredient which does not deleteriously affect palatability and appearance of foods is obtained by encapsulation of the mineral or vitamin in a grindable, glassy matrix composition. At least one edible oil is included in the encapsulating composition to prevent substantial adverse interaction between the mineral or vitamin encapsulant and the glass-forming matrix material, and to achieve controlled release of the encapsulant from the glassy matrix. The oil also reduces or eliminates the use of added water as a plasticizer thereby avoiding the need for substantial evaporation or drying to achieve a non-rubbery, grindable encapsulated ingredient. The oil assists in plasticizing the matrix material for extrudability and the prevention of undesirable browning or discoloration of the encapsulating matrix composition. The oil and the glassy matrix material provide a smooth mouthfeel and eliminate the rough, scratchy, gritty, dry, hard, or chalky mouthfeel associated with particulate or crystalline mineral sources. The fortification ingredient may be produced by melting the one or more glass-forming matrix components such as mono- or di-saccharides in the presence of optionally added water. The resulting melt may then be combined with an oil-slurried mineral and/or vitamin encapsulant and cooled to obtain a formable, pliable molten mass. The mass may be extruded and cut into pieces or pellets and cooled to obtain a grindable, glassy matrix which encapsulates the oil encapsulated mineral or vitamin. The encapsulated minerals and/or vitamins may be ground into a particulate composition such as a fine powder for direct incorporation into or for topical application onto foods such as ready-to-eat cereals, yogurt and fruit snacks.

45 Claims, 3 Drawing Sheets

U.S. PATENT DOCUMENTS

| | | | |
|---|---|---|---|
| 3,786,123 | A | 1/1974 | Katzen |
| 3,868,471 | A | 2/1975 | Decelles et al. |
| 3,922,354 | A | 11/1975 | Galluzzi et al. |
| 3,962,416 | A | 6/1976 | Katzen |
| 3,992,555 | A * | 11/1976 | Kovacs ................... 426/72 |
| 4,106,991 | A | 8/1978 | Markussen et al. |
| 4,178,392 | A | 12/1979 | Gobble et al. |
| 4,242,219 | A | 12/1980 | Bogerman et al. |
| 4,379,171 | A | 4/1983 | Furda et al. |
| 4,532,145 | A | 7/1985 | Saleeb et al. |
| 4,689,235 | A | 8/1987 | Barnes et al. |
| 4,816,259 | A | 3/1989 | Matthews et al. |
| 4,871,574 | A | 10/1989 | Yamazaki et al. |
| 4,886,820 | A | 12/1989 | Gross et al. |
| 4,888,171 | A | 12/1989 | Okonogi et al. |
| 4,999,208 | A | 3/1991 | Lengerich et al. |
| 5,009,900 | A | 4/1991 | Levine et al. |
| 5,023,083 | A | 6/1991 | Drell |
| 5,071,668 | A | 12/1991 | van Lengerich et al. |
| 5,075,058 | A | 12/1991 | Chan et al. |
| 5,079,012 | A | 1/1992 | Lengerich et al. |
| 5,087,461 | A | 2/1992 | Levine et al. |
| 5,118,513 | A | 6/1992 | Mehansho et al. |
| 5,183,690 | A | 2/1993 | Carr et al. |
| 5,431,929 | A | 7/1995 | Yatka et al. |
| 5,458,823 | A | 10/1995 | Perkins et al. |
| 5,466,460 | A | 11/1995 | McMahon et al. |
| 5,514,387 | A | 5/1996 | Zimmerman et al. |
| 5,597,416 | A | 1/1997 | Fuisz et al. |
| 5,683,720 | A | 11/1997 | Myers et al. |
| 5,744,180 | A | 4/1998 | Cherukuri et al. |
| 5,750,104 | A | 5/1998 | Sipos |
| 5,820,903 | A | 10/1998 | Fleury et al. |
| 5,851,553 | A | 12/1998 | Myers et al. |
| 5,862,998 | A | 1/1999 | Bogue et al. |
| 5,902,617 | A | 5/1999 | Pabst |
| 5,939,127 | A | 8/1999 | Abboud |
| 5,952,033 | A | 9/1999 | Anantharaman et al. |
| 5,958,502 | A | 9/1999 | Fulger et al. |
| 5,972,373 | A | 10/1999 | Yajima et al. |
| 5,972,404 | A | 10/1999 | van Lengerich |
| 5,972,415 | A | 10/1999 | Brassart et al. |
| 5,976,803 | A * | 11/1999 | Kota et al. ................... 426/74 |
| 6,004,594 | A | 12/1999 | van Lengerich |
| 6,008,027 | A | 12/1999 | Langner |
| 6,024,994 | A | 2/2000 | Jacobson et al. |
| 6,048,551 | A | 4/2000 | Amidon et al. |
| 6,149,965 | A | 11/2000 | van Lengerich et al. |
| 6,168,811 | B1 | 1/2001 | Clark et al. |
| 6,190,591 | B1 | 2/2001 | van Lengerich |
| 6,342,257 | B1 | 1/2002 | Jacobson et al. |

FOREIGN PATENT DOCUMENTS

| | | | |
|---|---|---|---|
| EP | 0 462 012 A2 | 12/1991 | |
| EP | 0 465 364 A1 | 1/1992 | |
| EP | 552057 A | 7/1993 | |
| EP | 603992 A1 | 6/1994 | |
| EP | 605913 A | 7/1994 | |
| GB | 15312 | 3/1911 | |
| JP | 47014316 A | 11/1972 | |
| JP | 59139317 A | 8/1984 | |
| JP | 1313421 A | 12/1989 | |
| JP | 6024962 A | 2/1994 | |
| JP | 2000139372 A | 5/2000 | |
| WO | WO 85/04074 | 9/1985 | |
| WO | WO 88/01512 A | 3/1988 | |
| WO | WO 91 03940 | 4/1991 | |
| WO | WO 92/00130 | 1/1992 | |
| WO | WO 92/00140 | 1/1992 | |
| WO | WO 92/12645 | 8/1992 | |
| WO | WO 94/23593 | 10/1994 | |
| WO | WO 95/00121 | 1/1995 | |
| WO | WO 95/18544 | 7/1995 | |
| WO | WO 95/26752 | 10/1995 | |
| WO | WO 96/09773 | 4/1996 | |
| WO | WO 96/14058 | 5/1996 | |
| WO | WO 97/16076 | 5/1997 | |
| WO | WO 97/38016 A | 10/1997 | |
| WO | WO 97/39116 | 10/1997 | |
| WO | WO 98/02148 A | 1/1998 | |
| WO | WO 98/09981 A | 3/1998 | |
| WO | WO 98/18610 | 5/1998 | |
| WO | WO 98/35704 A | 8/1998 | |
| WO | WO 98/50019 A | 11/1998 | |
| WO | WO 98/54980 | 12/1998 | |
| WO | WO 98/58642 A | 12/1998 | |
| WO | WO 99/11242 A1 | 3/1999 | |
| WO | WO 99/20745 A1 | 4/1999 | |
| WO | WO 99/23896 | 5/1999 | |
| WO | WO 99/34688 | 7/1999 | |
| WO | WO 99/45904 A1 | 9/1999 | |
| WO | WO 99/48372 | 9/1999 | |
| WO | WO 99/61002 A1 | 12/1999 | |
| WO | WO 99/65336 | 12/1999 | |
| WO | WO 00/21504 | 4/2000 | |
| WO | WO 00/41740 A2 | 7/2000 | |
| WO | WO 00/64436 A1 | 11/2000 | |

OTHER PUBLICATIONS

Lennart Randen et al., "Coprecipitation of Enzymes with Water Soluble Starch—An Alternative to Freeze–drying," *J. Pharm. Pharmacol.*, vol. 40, pp. 763–766 (1988).

Shigeaki Maruo et al., "Effects of Moranoline, 4–O–α–D–Glucopyranosylmoranoline and Their N–Substituted Derivatives on Thermostability of Cyclodextrin Glycosyltransferase, Glucoamylase, and β–Amylase," *Biosci. Biotech. Biochem.*, vol. 57, No. 8, pp. 1294–1298, (1993).

Wendell Q. Sun et al., "Protein stability in the amorphous carbohydrate matrix: revelevance to anhydrobiosis," *biochimica et Biophysica Acta*, vol. 1425, pp. 245–254 (1998).

Colonna et al., "Extrusion Cooking of Starch & Starchy Products," *Extrusion Cooking*, C. Mercier, et al. AACC, St. Paul, MN (1989), pp. 247–319.

Meuser et al., "A Systems Analytical Approach To Extrusion," *Food Extrusion Science & Technology*, ed. J. Kokini, Dekker Publ. (1992), pp. 619–630.

Brochure entitled "Innovate With Raftiline®," Orafti Active Food Ingredients, Nov. 1996.

"Inulin–A 'Good–for–you' Fat Replacer, Texture Modifier," *Food Formulating*, p. 15, Feb. 1997.

Brighenti, F., et al., "One Month Consumption of Ready–to–eat Breakfast Cereal Containing Inulin Markedly Lowers Serum Lipids in Normolipidemic Men,", from: Proceedings of 7th FENS European Nutrition Conference, Vienna, 1995.

Silva, R., "Use of Inulin as a Natural Texture Modifier," *Cereal Foods World*, Oct. 1996, vol. 41, No. 10, pp. 792–794.

* cited by examiner

PRODUCTION OF OIL ENCAPSULATED MINERALS AND VITAMINS IN A GLASSY MATRIX

FIELD OF THE INVENTION

The present invention relates to encapsulated minerals and encapsulated vitamins for use as an ingredient for the fortification of foods. The present invention also relates to methods for making the encapsulated mineral and vitamin ingredients and to food products, such as yogurt and ready-to-eat cereals, containing it.

BACKGROUND OF THE INVENTION

The fortification of foods with minerals such as calcium, iron, magnesium, zinc, and selenium or vitamins, such as vitamin C to achieve a Recommended Daily Allowance (RDA) generally results in textural, taste, odor, color, separation, or inactivation, problems in the foods. Processing problems may also occur due to the presence of large amounts of minerals or vitamins in food compositions. In the fortification of foods with calcium, the low solubility of many calcium compounds, particularly the ones which are the more economical to employ, leads to low absorption into the blood stream as well as difficulty in their incorporation into foods. Calcium compounds tend to impart a chalky, gritty mouthfeel, off-flavors, and undesirable browning or discoloration. In addition, the form of calcium or the interaction, reaction, or complexing of calcium with proteins or other food components, during storage, or during heating or cooking in the preparation of the food may hinder or substantially prevent its absorption into the bloodstream or produce undesirable side-products.

Calcium plays an important role in blood coagulation, nerve transmission, muscle contraction, and heart function. Protection against high blood pressure, colon cancer, and the degenerative bone disease known as osteoporosis have been attributed to calcium. Approximately one percent of the body's calcium circulates in the blood and the rest is present in bones and teeth. The U.S. Recommended Daily Allowance (RDA) of calcium is 1000 mg for adults and children 12 or more years of age. The RDA for pregnant and lactating women is 1200 mg. However, the average calcium intake is only about one-third of the required daily allowance. If dietary sources of calcium do not provide sufficient amounts of calcium to the blood, calcium is depleted from the bones to compensate for the insufficient amounts. Age related bone loss and fracture rates in patients with osteoporosis may be reduced with high dietary intake of calcium.

The ability of different individuals to utilize the calcium in food may vary considerably. For example, a high protein diet may result in about 15% of the dietary calcium being absorbed. A low protein diet may result in only about 5% of the dietary calcium being absorbed. Phytic acid in cereal grains interferes with calcium absorption by forming insoluble calcium phytate in the intestine. Oxalates in foods, such as spinach and rhubarb, may similarly interfere with calcium absorption.

Other intestinal factors that influence the absorption of calcium include pH, the calcium:phosphorus ratio, the presence of free fatty acids which occurs when fat absorption is impaired, and the amount of vitamin D. Generally, the more alkaline the contents of the intestines, the less soluble are the calcium salts. Also, a high calcium:phosphorus ratio favors the formation of tricalcium phosphate rather than the more soluble, better absorbed forms. If either calcium or phosphorus is taken in excess, excretion of the other is increased. The optimal ratio is 1:1 when the intake of vitamin D is adequate. On the other hand, vitamin D promotes the absorption of calcium from the intestine.

Although milk has been a major source of calcium for infants and young children, many teenagers and adult Americans are consuming lesser amounts of it. The calcium content of milk and other beverages may be increased to facilitate meeting of the U.S. RDA for calcium.

For example, calcium enrichment or fortification of milk is disclosed in U.S. Pat. Nos. 2,871,123, 4,701,329, 4,840, 814, and 4,851,243. In U.S. Pat. No. 2,871,123 calcium carbonate is used as a calcium source in the production of a canned calcium-enriched concentrated milk product for dilution to make infant formula. Carrageenan gum is used for suspension of the calcium carbonate. U.S. Pat. Nos. 4,701,329 and 4,851,243 disclose the production of calcium-enriched and phosphorus- enriched fortified milk by the addition of tri-basic calcium phosphate, carrageenan and guar gum to fresh milk, effecting hydration of the gums, and assuring uniform distribution of the added materials in the milk. U.S. Pat. No. 4,840,814, discloses the preparation of calcium-enriched milk or toned milk by adding a water soluble calcium salt of an organic acid to thermally sterilized milk or toned milk, and adjusting the pH value of the obtained mixture to 6.6 or above.

Beverages and beverage concentrates nutritionally supplemented with solubilized calcium are disclosed in U.S. Pat. Nos. 4,737,375 and 4,740,380. In U.S. Pat. No. 4,737, 375 the beverages and concentrates are substantially free of a sugar alcohol and contain specified levels of total edible acids selected from mixtures of citric, malic and phosphoric acid. U.S. Pat. No. 4,740,380 discloses a clear, calcium-fortified aqueous acidic beverage. The beverage comprises an aqueous solution of an organic calcium compound such as calcium gluconate at a pH of about 4 and below wherein the calcium compound content does not exceed the solubility limit of the compound in water. An inorganic calcium salt can be used alone or in combination with an organic calcium compound to form an acidic beverage provided the pH is adjusted with an organic acid.

However, when incorporating calcium into liquids, the source of calcium, usually an inorganic salt in finely divided form, tends to settle out upon extended storage. Also, the use of soluble sources of calcium or even the use of suspended sources of calcium tends to result in off flavors, adverse appearance, and undesirable increases in viscosity. Generally, the more soluble the salt or the more finely divided it is so as to improve suspendability, the quicker or more easily its taste will be detected. Also, solubilization of the calcium increases the likelihood of it being complexed with or interacting with other components of the beverage or of other foods consumed with it. The complexation or interaction of the calcium may result in it being less susceptible to absorption into the blood.

U.S. Pat. No. 4,676,583 discloses the production of an aseptic calcium-enriched soy bean curd by adding a calcium hydroxide-sucrose complex as coagulant to the soy bean milk, sterilizing the resulting mixture by heating, adjusting the pH value of the sterilized product to weakly acidic, charging the sterilized product into a container under an aseptic condition and sealing the opening of the container. The calcium hydroxide-sucrose complex is coagulated with the soybean milk by heating. When the calcium hydroxide-sucrose complex used as coagulant is insufficient to provide the required extent of calcium enrichment, calcium lactate may be added in an aseptic atmosphere after the sterilization process at the time of pH adjustment.

Calcium compounds have been utilized in baked goods, such as crackers, as components of leavening agents, pH adjusters, yeast foods, and for their nutritive value. U.S. Pat. No. 4,196,226 discloses a leavening acid comprising alkali metal aluminum phosphate granules having a calcium rich outer surface for improving flow and dusting properties. The product may be used as a leavening acid in moist doughs, and liquid batters such as pancake batters. U.S. Pat. No. 4,678,672 to Dartey et al discloses the use of calcium and ammonium carbonates and bicarbonates in leavening systems for the production of reduced calorie crackers. Various emulsifiers are disclosed as replacements for fat. Magnesium and/or calcium carbonates are taught as acid-neutralizing constituents in British patent 335,214 for dough or flour compositions which contain persulphates and bromates. Calcium carbonate is disclosed as a bread improver in U.S. Pat. No. 2,970,915. It is also taught as a buffering agent for a liquid yeast brew in U.S. Pat. No. 3,490,916. The dough-up stage addition of calcium carbonate for its nutritive value in the production of reduced fat or no-added fat crackers, is disclosed in U.S. Pat. No. 5,108,764 to Craig. U.S. Pat. Nos. 4,859,473 and 5,066,466 to Arciszewski et al disclose the addition of calcium carbonate to the dough-up stage for its nutritive value in the production of low sodium crackers. U.S. Pat. No. 5,514,387 to Zimmerman et al discloses the use of an emulsifier system to substantially increase the calcium content of crackers and other baked goods without adversely affecting texture of the baked goods.

Calcium fortification of yogurt is disclosed in U.S. Pat. Nos. 4,784,871, 5,449,523, and 5,820,903. According to U.S. Pat. No. 4,784,871 a calcium fortified yogurt is produced by adding an acid soluble calcium salt to fruit flavoring which is subsequently combined with a yogurt base. Sugar is added to the fruit to assist in the avoidance of lumping of calcium phosphate. The fruit is employed to solvate a portion and to suspend the balance of the insoluble calcium within the yogurt product. In the process of U.S. Pat. No. 5,449,523 chelating agents are added to avoid undesirable milk protein precipitation. Usage of such chelating agents, however, contribute an undesirable flavor to the yogurt at the high levels necessary to fortify to 1000 mg calcium. U.S. Pat. No. 5,820,903 discloses preparing a fermented dairy product, such as yogurt, fortified with calcium that is visually undetectable in the final product. The process involves the post fermentation addition of a source of insoluble calcium phosphate having a particle size of less than 150 microns. Sufficient amounts of calcium phosphate of the requisite particle size are added with minimal shear to the fermented dairy product to provide a total calcium content of a maximum of 1500 mg of calcium per 227 g of product. The calcium phosphate salt is admixed with a liquid carrier to form a slurry comprising about 30 to 40% calcium phosphate.

In U.S. Pat. No. 4,765,996 polished rice or barley is enriched with nutrients which are fixed in and on the grain by coating an oil/fat and/or a wax on the grains, coating the same with a hydrophilic emulsifier and further coating them with a starch-based coating agent.

Mineral and vitamin fortification of high fiber, ready-to-eat cereals with minerals such as calcium and iron, and vitamins such as the B vitamins is disclosed in International patent publication no. WO 99/34688, published Jul. 15, 1999. The cereals are fabricated from cooked cereal doughs containing high levels of soluble fiber supplied at least in part by inulin or other β-2-1-fructofuranose materials.

As disclosed in International patent publication no. WO 99/34688, as well as in U.S. Pat. No. 4,871,574, inulin is known for use as a prebiotic, that is, a food material that is metabolized in the intestine by desirable bacteria such as *bifidus and lactobacillus*. The promotion of desirable intestinal flora, it is taught, is thought to be related to a variety of health benefits. The lowering of blood lipids by consumption of inulin is reported in Brighenti et al, "One Month Consumption of Ready-to-Eat Breakfast Cereal Containing Inulin Markedly Lowers Serum Lipids in Normolipidemic Men," *Proceedings of 7$^{th}$ FENS European Nutrition Conference*, Vienna, 1995. The use of inulin as a fat replacer in cookie cream fillings is disclosed in U.S. Pat. No. 5,939,127. Health benefits of inulin as well as its use as a fat replacer are reported in: a) "Inulin-A 'Good-for-you' Fat Replacer, Texture Modifier," *Food Formulatina*, p 15 (February 1997), b) "Innovate with Raftiline," published by Orafti Active Food Ingredients, Tienen Belgium, doc. B1-60, edited by P. Coussement (11/96), and c) Silva, R. F., "Use of Inulin as a Natural Texture Modifier," *Cereal Foods World*, American Assoc. of Cereal Chemists, vol. 41, no. 10, pp 792–794 (October 1996).

However, as disclosed in International patent publication no. WO 99/34688 fiber, especially insoluble fiber, may adversely affect selected mineral and vitamin absorption. Accordingly, the cereals are fortified with bioavailable sources of calcium and other minerals and vitamins. The mineral fortifiers may be incorporated into the cereal compositions directly, and vitamins are preferably topically applied.

Other food compositions which contain inulin and minerals or vitamins are disclosed in U.S. Pat. Nos. 5,952,033 and 5,972,415. The production of gelatinized cereal products which may be used as a pet food or breakfast cereal is disclosed in U.S. Pat. No. 5,952,033. A starch source, a protein source, a plant material which is a source of inulin, and water are heated to gelatinize the starch. The matrix making up the cereal product must be gelatinized to remove or destroy the sesquiterpene compounds present in the inulin-containing plant material to reduce bitter flavors and palatability problems. In making a simulated pet food, an emulsion is formed and additional ingredients such as sugars, salts, spices, and minerals may be added to the emulsion. The final product has the appearance and texture of meat. U.S. Pat. No. 5,972,415 discloses a nutritive composition based upon fibers which is prepared by mixing pea fibers and inulin in demineralized water at 65° C. to 70° C., subjecting the mixture to a colloid mill, then combining it with a pre-emulsion to form a mixture and subjecting the mixture to a colloid mill. The resulting emulsion is admixed with carbohydrates, a protein mixture, minerals and vitamins. The composition is then heat treated at 150° C. and stored.

However, the processes of U.S. Pat. Nos. 5,952,033 and 5,972,415 employ substantial amounts of water, and do not prevent adverse interaction between the inulin and minerals. Also, the products obtained tend to be rubbery or creamy and are not easily grindable into fine particulate compositions or powders for incorporation into other foods.

The encapsulation of minerals and vitamins in plasticizable matrices is disclosed in International Patent Publication No. WO 98/18610 (published May 7, 1998) and International Patent Publication No. WO 99/48372 (published Sep. 30, 1999) each to van Lengerich. In the process of International Patent Publication No. WO 98/18610 the plasticizable matrix material, such as starch, is admixed with at least one plasticizer, such as water, and at least one release-rate controlling component under low shear mixing conditions to plasticize the plasticizable material without substantially destroying the at least one plasticizable material and to obtain a substantially homogeneous plasticized mass. The plasticizer content is substantially reduced and the temperature of the plasticized mass are substantially reduced prior to admixing the plasticized mass with the encapsulant to avoid substantial destruction of the encapsulant and to obtain a formable, extrudable mixture.

Production of an edible composition that has a chewable texture and has at least one encapsulated component is disclosed International Patent Publication No. WO 99/48372. A free-flowing mixture, such as ground cookies and a plasticizer such as oil and water are mixed with an encapsulant to obtain a formable dough or crumbly mass. The dough is shaped or formed into pieces or pellets and dried to a shelf-stable moisture content. The processing is conducted at a temperature sufficiently low so as to prevent thermal degradation of the encapsulant and pressures sufficiently high to enable the formation of coherent pieces. The encapsulant may be vitamins and minerals such as calcium, selenium, magnesium salts, available iron, and iron salts. Soluble or insoluble fiber may be included to control release of encapsulant. Hydrophobic components, it is disclosed may be employed to help prevent or delay penetration of water or gastric juice into the matrix by repelling water or aqueous acids thereby delaying release of the encapsulant into the surrounding media. The amount of active component or encapsulant which is incorporated into the products may be such so as to provide or deliver an effective amount of the active component at its intended location, such as the small intestine.

Encapsulation of components in a plasticizable matrix to achieve a plasticized mass or an extrudable consistency, using substantial amounts of a plasticizer such as water, generally results in a pliable, chewable, or rubbery texture in the plasticized composition. To achieve a solid, or readily grindable consistency would entail removal of the plasticizer.

Encapsulation of components in a grindable, glassy carbohydrate matrix is disclosed in U.S. Pat. Nos. 5,009,900 and 5,087,461 to Levine et al, and U.S. Pat. Nos. 5,972,404 and 6,004,594 each to van Lengerich. In U.S. Pat. Nos. 5,009,900 and 5,087,461 to Levine et al volatile and/or labile components, such as vitamins or flavoring components, are encapsulated in extruded glassy matrices comprising a water-soluble, chemically-modified starch having a dextrose equivalent not greater than about 2, a maltodextrin having a dextrose equivalent in the range of from about 5 to about 15, corn syrup solids or a polydextrose having a dextrose equivalent in the range of from about 21 to about 42, and a mono- or disaccharide. U.S. Pat. Nos. 5,972,404 and 6,004,594 disclose encapsulation of an emulsifier in a low molecular weight carbohydrate in powder form rather than in a conventional shortening component. Low molecular weight carbohydrates which may be employed are mono- or di-saccharides, maltodextrins having a dextrose equivalent (DE) in the range of about 4 to 20, and corn syrup solids or polydextrose having a dextrose equivalent in the range of about 21 to about 97. Lower concentrations of emulsifiers, it is disclosed, provide comparable emulsifier performance by virtue of enhanced dispersion of the emulsifier.

International Patent Publication No. WO 99/65336 to Clark et al (published Dec. 23, 1999 discloses that the use of encapsulants or coating agents to mask or reduce the disagreeable sensory characteristics associated with fortification so as to prevent interaction of the fortificants with the senses is not cost effective. Coating agents, it is disclosed are expensive and the encapsulation process can use spray drying or fluid bed granulating which requires high energy use. In the process of WO 99/65336, fortificant particles are agglomerated with a binding/masking agent and the particles are added to an edible composition, such as a ready-to-eat cereal. The agglomeration reduces the surface area, dispersibility and solubility of the fortificants such as calcium, zinc, iron or other transition metals, or vitamins.

In the present invention, the concentration of minerals and vitamins in foods is substantially increased to provide Recommended Daily Allowances (RDA) without adversely affecting color, texture, taste, odor, or other sensory characteristics of food compositions such as ready-to-eat cereals, and yogurt. The fortification of foods with minerals such as calcium, iron, magnesium, zinc, and selenium or vitamins, such as vitamin C to achieve a Recommended Daily Allowance (RDA) is achieved without processing, separation or activation problems in the foods. The encapsulated mineral and vitamin compositions of the present invention may be produced without substantial amounts of water, and without substantial adverse interaction between the encapsulant and the encapsulating matrix composition. The encapsulated products are non- rubbery and readily grindable into fine particulate compositions or powders for incorporation into or onto food compositions. In accordance with the methods of the present invention, an encapsulated product may be obtained by extrusion without the need for removal of substantial amounts of plasticizer, such as water, and without the need for plasticizing or gelatinizing starch.

In accordance with embodiments of the present invention, the fiber content of foods may be increased, and the palatability of minerals and vitamins is increased without adversely affecting mineral and vitamin absorption. In the fortification of foods with calcium, absorption of calcium into the blood stream is substantially enhanced by encapsulating matrix compositions of the present invention. Fortification of foods such as ready-to-eat cereals and yogurt with Recommended Daily Allowances (RDA) of calcium, iron, selenium, copper, magnesium, zinc, and other minerals and vitamins is obtained without imparting a chalky, gritty mouthfeel, off-flavors, and undesirable browning or discoloration. Adverse interaction, reaction, or complexing with proteins or other food components, or oxidation agents such as oxygen during storage, or during heating or cooking in the preparation of the food so as to hinder or substantially prevent its absorption into the bloodstream or produce undesirable side-products are avoided with the methods and compositions of the present invention.

SUMMARY OF THE INVENTION

The present invention provides a non-rubbery, particulate, ground or powdered mineral and/or vitamin fortification ingredient which exhibits a smooth mouthfeel, and masks undesirable odor, off-flavors, and scratchy or excessively gritty texture attributes of the encapsulant. It may desirably provide a slight or substantial degree of sweetness, and is readily dispersible in foods without discoloring the foods. In embodiments of the invention, the fortification ingredient increases the fiber content of foods without adversely affecting mineral and vitamin absorption, and provides a controlled release of the encapsulant.

The fortification ingredient may be produced by encapsulating a mineral, such as iron or calcium, or a vitamin, such as vitamin C, in a glassy matrix. An encapsulant component comprising at least one mineral or vitamin is admixed with an edible oil to obtain a slurry wherein the oil encapsulates the mineral or vitamin. The slurry is admixed with a melt comprising at least one molten glass-forming matrix component, such as mono- and di-saccharides, maltodextrins, dextrins, and oligosaccharides such as fructooligosaccharides or inulin, to obtain a molten blend. The molten blend is cooled to obtain a formable, pliable mass. The formable, pliable mass may be extruded and cut into pieces or pellets and cooled to obtain a grindable, glassy matrix which encapsulates the oil encapsulated mineral or vitamin. In embodiments of the invention, further size reduction of the cut pieces may be performed by grinding the glassy matrix into a fine powder. The grindable, non-rubbery fortification ingredient may be obtained without the need for starch gelatinization or substantial moisture reduction steps.

To increase load levels of the mineral or vitamin encapsulant in the fortification ingredient, an additional amount of the encapsulant component may be admixed with the glass-forming matrix component. The glass-forming matrix component is heated in the presence of the additional encapsulant component to form the melt which is then combined with the oil slurried encapsulant component. In forming the melt, water may be admixed with the glass-forming matrix component to at least partially dissolve or plasticize the glass-forming matrix component. Heating of the glass-forming matrix component in the presence of the water facilitates formation of the melt and reduces its viscosity for easier mixing with the oil slurry. In embodiments of the invention, at least one glass-forming mono- or di-saccharide, and/or glass-forming polysaccharides, such as maltodextrins and dextrins, and glass-forming oligosaccharides may be included in the glassy matrix composition by preblending of dry ingredients to form a dry mix prior to admixture with the oil slurry.

In the fortification of foods with calcium, absorption of calcium into the blood stream is substantially enhanced by a glass-forming oligosaccharide matrix material such as fructooligosaccharides and inulin. In addition, medium chain triglycerides (MCT) may be employed as the edible oil component to also substantially enhance the absorption of calcium into the blood. Lactose may also be used as a glass-forming matrix component to also enhance calcium absorption into the blood stream. Fortification of foods such as ready-to-eat cereals and yogurt with at least 100% of the Recommended Daily Allowances (RDA) of calcium, iron, selenium, copper, magnesium, zinc, and other minerals and vitamins is obtained without imparting a chalky, gritty mouthfeel, off-flavors, and undesirable browning or discoloration. Adverse interaction, reaction, or complexing with proteins or other food components, or oxidation agents such as oxygen during storage, or during heating or cooking in the preparation of the food so as to hinder or substantially prevent its absorption into the bloodstream or produce undesirable side-products are avoided. In embodiments of the invention, the elemental calcium content of the fortification ingredient may be about 15% by weight to about 32% by weight, based upon the total weight of the glass-forming matrix component.

DETAILED DESCRIPTION OF THE INVENTION

Figure 1:
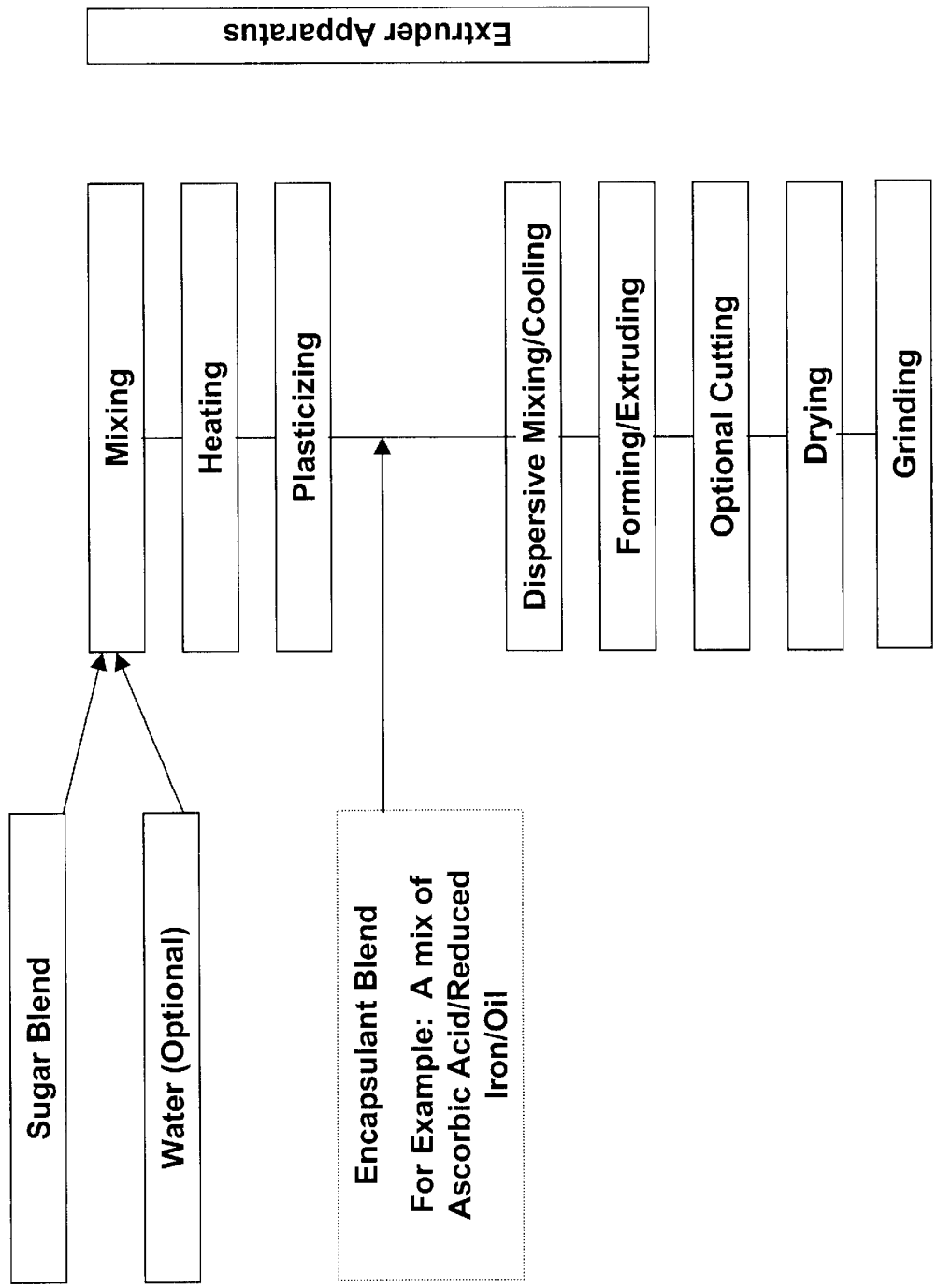
FIG. 1 shows a schematic representation of the process of the present invention.

The mineral and vitamin content, such as the iron or calcium content of foods such as ready-to-eat cereals, yogurt and fruit snacks, is substantially increased without deleteriously affecting palatability and appearance of the foods in accordance with the present invention by encapsulation of the mineral or vitamin in a grindable, glassy matrix composition. The encapsulated minerals may be ground into a particulate composition such as a fine powder for direct incorporation into or for topical application onto the foods. The glassy matrix composition may include mono- and di-saccharides, polysaccharides such as maltodextrins and dextrins, and oligosaccharides, such as $\beta$2-1 fructofuranose materials, preferably fructooligosaccharides (FOS) and inulin, which not only forms a glassy matrix, but also beneficially increases the fiber content of the food.

At least one edible oil is included in the encapsulating composition. The oil helps to prevent substantial adverse interaction between the mineral or vitamin encapsulant and the glass-forming matrix material during and after the encapsulation. Control of release of the encapsulant from the glassy matrix is also provided by the oil. Little, if any, water is employed for plasticization thereby avoiding the need for substantial evaporation or drying to achieve a non-rubbery, grindable encapsulated ingredient. The oil assists in plasticizing the matrix material for extrudability, the avoidance of extruder surging, and the prevention of undesirable browning or discoloration of the encapsulating matrix composition during encapsulation, during incorporation into the food, and during manufacturing, processing, heating or cooking, or storage of the food. It is believed that the oil forms an inner layer which coats or encapsulates the mineral or vitamin particle and separates it from the outer, glass-forming matrix composition which encapsulates the oil-coated particles. The oil and the glassy matrix material provide a smooth mouthfeel and eliminate the rough, gritty, dry, hard, or chalky mouthfeel associated with particulate or crystalline mineral sources such as iron or calcium salts. The encapsulation delays release of the encapsulant to the small intestines rather than in the mouth or stomach thereby alleviating taste and texture problems while enhancing absorption in the blood.

In the fortification of foods with minerals which are peroxidants, such as iron, magnesium, copper, and zinc, a saturated fat, such as a fractionated milk fat may be employed to reduce or prevent oxidation and rancidity. Also, an antioxidant, such as ascorbic acid may be included as an encapsulant to reduce or preclude oxidative effects.

In the fortification of foods with calcium, absorption of calcium into the blood stream is substantially enhanced by a glass-forming oligosaccharide matrix material such as fructooligosaccharides and inulin. In addition, medium chain triglycerides (MCT) may be employed as the edible oil component to also substantially enhance the absorption of calcium into the blood. In embodiments of the invention, lactose may be used as a glass-forming matrix component to enhance calcium absorption into the blood stream. Calcium absorption is enhanced, it is believed by creation or promotion of an acidic medium, or lowering of the pH by these components in the small intestine.

In embodiments of the present invention the calcium level of ready-to-eat cereals may be increased from approximately 0–3% (not including calcium from milk) of U.S. RDA per 27 gram serving or reference amount to a product containing more than 50%, preferably at least 100% of U.S. RDA of 1000 mg calcium in a 27 gram serving or reference amount (not including calcium from milk). Similar levels of calcium or other mineral or vitamin enrichment (e.g. at least 100% of U.S. RDA) may also be achieved in other foods such as yogurt. For example, the calcium level of yogurt may be increased from approximately 20–25% of U.S. RDA per 170 gram serving or reference amount to a product containing at least 100% of U.S. RDA of 1000 mg calcium in a 170 gram serving or reference amount.

Oligosaccharides, such as oligofructose, fructooligosaccharides, inulin, and sources thereof which may be employed as glassy matrix components in accordance with the present invention are disclosed, for example, in: 1) International patent publication no. WO 99/34688, 2)U.S. Pat. No. 4,871,574, 3) U.S. Pat. No. 5,431,929,4) U.S. Pat. No. 5,939,127,5) "Inulin-A 'Good-for-you' Fat Replacer, Texture Modifier," *Food Formulatinc*, p 15 (Febuary 1997), 6) "Innovate with Raftiline," published by Orafti Active Food Ingredients, Tienen Belgium, doc. B1-60, edited by P. Coussement (November 1996), and 7) Silva, R. F., "Use of Inulin as a Natural Texture Modifier," *Cereal Foods World*, American Assoc. of Cereal Chemists, vol. 41, no. 10, pp 792–794 (October 1996), the disclosures of which are herein incorporated by reference in their entireties.

Inulin is a well known β-2-fructofuranose material long used as a food supplement and a staple of commerce. It is a carbohydrate material derived from a variety of crops importantly from Jerusalem artichoke and chicory. Inulin is a prebiotic, that is, a food material that is metabolized in the intestine by desirable bacteria such as *bifidus and lactobacillus*.

Generally, inulin is the clean, dried fibrous material which is separated by extraction from, for example, chicory, onions and Jerusalem artichokes and other common plant sources. Inulin is available in various commercial grade varieties. Pure inulin is commercially available from, for example, Rhone-Poulenc in the U.S. under the trade name RAFTILINE® and from Imperial Suicker Unie, LLC in Europe. Pure inulin has an average degree of polymerization ("DP") of about 9 to 10. Raftiline, available in powder form, is obtained from chicory roots and is a mixture of $GF_n$ molecules where: G=glucose, F=fructose, and n=number of fructose units linked and ranges from about two to more than 50. Less preferred for use herein are less pure inulin source materials such as dried Jerusalem artichoke flour, deflavored onion flour and mixtures thereof.

Also useful herein are oligofructose materials available under the RAFTILOSE trade name from Rhone-Poulenc. Such materials are plant derived and may have a DP of about 2–9, i.e., with fructose chains of up to about nine, generally up to about 7 fructose units. RAFTILOSE, being a hydrolysis product from RAFTILINE, is composed of shorter length molecules of $GF_n$ (glucofructosans) and $F_m$ (fructosans) where "n" and "m" are about 2 to 9. RAFTILOSE is available from the supplier in both syrup and powder forms. Four versions of RAFTILOSE are available, RAFTILOSE 30, 60, 85 and 95. The names indicate different levels of hydrolysis. For example, RAFTILOSE 95 contains 95% oligofructose units and 5% sugars (glucose, fructose and sucrose). RAFTILOSE 95, a preferred oligofructose for use herein, is most commonly available in its powder form, but is also available as a syrup. RAFTILOSE 30, 60 and 85 are most commonly available as syrups. RAFTILINE, the inulin material, is only available in a powdered form. Another RAFTILOSE-type oligosaccharide composition which may be employed in the present invention is Synergy-1 which is produced by Rhone-Poulenc, the same supplier of RAFTILOSE.

RAFTILOSE P-95 is a mixture of oligosaccharides which comprise fructose units linked together by ←(2–1) linkages. A portion of these polymers are terminated by a glucose unit. The total number of fructose or glucose units (=Degree of Polymerization or DP) of chicory inulin ranges between 2 and 8 with a mean of DP=4. The oligofructose content of RAFTILOSE P-95 is about 88.4% by weight to about 92.2% by weight. The total glucose, fructose, and sucrose content is from about 2.85% by weight to about 6.65% by weight. It is a fine, white powder and has a moisture content of less than or equal to 5% by weight and a pH of about 5.0 to 7.0.

In still other useful variations, manose can be substituted for the fructose in full or partial substitution, i.e., oligomanans. In still other useful variations, other oligomers can be used with similar degrees of polymerization that are from monomers of monosaccharides, selected from the group consisting of glucose, xylose, aribinose, and mixtures thereof (i.e., DP 2–60).

The β-2-fructofuranose material useful herein includes oligomers and polymers thereof. Particularly useful in terms of cost and availability are inulin and fructoogliosaccharides ("FOS") and mixtures thereof.

FOS materials are also available commercially such as from GTC Nutrition Company, Westminster, CO. FOS materials have an average degree of polymerization ("DP") ranging from about 2–4 polyfructans. Due to their lower molecular weight, the FOS materials have a greater solubility in water. FOS materials have a slight sweetness to their taste. A further advantage is that the FOS materials when topically applied form a clear, almost undetectable coating. As a result, FOS materials are especially suitable for topical application.

Where in the balance of the present description the use of inulin is described, other β-2 fructofuranose materials described above can be used in full or partial substitution for the particular inulin materials described as can be other oligosaccharides, e.g., oligomanans.

In embodiments of the present invention glass-forming mono- and/or di-saccharides are employed alone or in combination with each other or with other glass-forming matrix materials. Exemplary mono- and di-saccharides which may be employed are lactose, glucose, dextrose, sucrose, fructose, maltose, and mixtures thereof. Lactose is preferred for its enhancing effect upon the absorption of calcium into the blood stream. Each of the glass-forming matrix materials such as the mono- and di-saccharides, the polysaccharides, and the oligosaccharides may be employed in process-compatible amounts which do not adversely affect viscosity of the molten matrix composition or color of the encapsulated products. Exemplary amounts of each mono- and di-saccharide may range up to about 100% by weight, generally up to about 50% by weight, based upon the total weight of the glass-forming matrix materials. For example, in embodiments of the present invention, the amount of lactose may be up to about 100% by weight, based upon the total weight of the glass-forming matrix materials. In other embodiments the weight ratio of lactose to the total amount of other mono- and di-saccharides may range from about 5:95 to about 50:50.

In other embodiments of the present invention, other process compatible, glass-forming polysaccharides, such as maltodextrins and dextrins may be included in the glassy matrix composition. Exemplary amounts of these glass-forming components may range up to about 100% by weight, generally up to about 50% by weight, for example up to about 10% by weight, based upon the total weight of the glass-forming matrix materials. Generally, for the encapsulation of calcium in a glassy matrix, polysaccharides such as maltodextrins and dextrins, and starches are less preferred because, unlike the oligosaccharides such as inulin, and lactose they do not contribute to the enhancement of calcium absorption into the blood.

The mineral and/or vitamin components which may be encapsulated in accordance with the present invention include edible acidic, neutral or basic inorganic or organic salts of minerals such as calcium, copper, iron, magnesium, zinc, such as zinc oxide, and selenium, or vitamins, such as vitamin A, C, D, B vitamins, such as riboflavin, vitamin $B_6$, vitamin $B_{12}$ thiamin, niacin, phosphorus, folic acid or folate sources, and mixtures thereof.

The calcium component may be one or more edible acidic, neutral or basic inorganic or organic salts such as calcium carbonate, tricalcium phosphate, calcium phosphate, calcium hydrogen phosphate, calcium dihydrogen phosphate, calcium hydroxide, calcium citrate, calcium malate, calcium lactate, calcium acetate, calcium ascorbate, calcium chloride, calcium gluconate, calcium hydroxide, calcium oxide, dicalcium phosphate, monocalcium phosphate, calcium phosphate monobasic calcium phosphate dibasic, calcium phosphate tribasic, calcium pyrophosphate, calcium sulfate, and mixtures thereof. Low solubility of the calcium component is preferred to reduce the risk of undesirable complexation or interaction with matrix components such as fructooligosaccharides and sugars, or with food components such as gluten or other proteins which may cause browning or hinder machinability or which may reduce absorption of the calcium into the blood. Also, low solubility of the calcium component reduces its dissolution in the mouth during consumption of the food product which reduces the detection of any off-flavors. The source of calcium for providing calcium enrichment to the food products of the present invention is preferably an insoluble, tasteless or bland, alkaline calcium salt or compound which does not adversely affect pH, flavor, or color of the food product. Exemplary of edible, bland, insoluble calcium components which may be used in preferred embodiments of the invention are calcium carbonate, tricalcium phosphate, and mixtures thereof. Calcium carbonate is the most preferred calcium component for enriching the calcium content of ready-to-eat cereals and yogurt in accordance with the present invention.

A source of calcium carbonate which may be employed is ground, food grade limestone. The ground limestone may have a calcium carbonate content of at least about 94% by weight. It is generally obtained by crushing, grinding and classifying naturally occurring limestone (calcite), benefitted by flotation and/or air classification. It is a white to off-white, microcrystalline powder, odorless, tasteless and stable in air. It is insoluble in water and alcohol. It is soluble in dilute acetic acid, dilute hydrochloric acid and in nitric acid. The ground limestone, as well as other calcium compounds utilized in the present invention, may have a particle size distribution of: a) less than or equal to about 0.2% by weight retained on a 200 mesh U.S. Standard Sieve, and b) at least about 90% by weight, preferably at least about 98% by weight, passing through a 325 mesh U.S. Standard Sieve.

Exemplary of other calcium components and their particle size distributions which may be employed are:

| Calcium Source | Bulk Density (loose) g/cc | Mean Particle Size, $\mu$ | Particle size distribution ($\mu$) |
| --- | --- | --- | --- |
| Calcium Carbonate (Omyacal FG-10) | 0.8 | 13.9 | $10^{th}$ percentile < 2.21<br>$50^{th}$ percentile < 11.2<br>$90^{th}$ percentile < 30.2 |
| Tricalcium Phosphate-High Density (Gadot) | 0.3–0.5 | 26.5 | $10^{th}$ percentile < 6.94<br>$50^{th}$ percentile < 22.6<br>$90^{th}$ percentile < 51.3 |

The amount of the calcium enrichment component, such as calcium carbonate, for providing 100% of the U.S. RDA of 1000 mg of calcium per serving may be at least about 10% by weight, preferably greater than about 20% by weight, most preferably at least about 25% by weight, up to about 80% by weight, preferably up to about 55% by weight, more preferably up to about 35% by weight, for example from about 15% by weight to about 32% by weight of elemental calcium, based upon the total weight of the mono- and di-saccharides, and the oligosaccharides such as fructooligosaccharides, and inulin. Increasing the amount of elemental calcium, based upon the total weight of oligosaccharides, tends to result in difficulty in pumping of a calcium/oil slurry, poor dispersion of the oligosaccharides, extruder surging, browning of the oligosaccharides, oily products, or off-flavors. Generally, about five (5) grams of the encapsulated calcium products of the present invention provide 100% of the U.S. RDA of 1000 mg of calcium per serving. Similar fortification or enrichment levels may be achieved with other minerals and vitamins. For example, the amount of encapsulant such as iron and/or ascorbic acid may be up to about 35% by weight. In embodiments of the invention where the U.S. RDA for a mineral or vitamin is low, the loading level of the encapsulant may be low, such as from about 0.5% by weight to about 10% by weight, based upon the weight of the glass-forming matrix ingredient.

Oleaginous compositions which may be used to obtain the encapsulated fortificants of the present invention may include any known shortening or fat blends or compositions useful for food applications, and they may include conventional food-grade emulsifiers. Vegetable oils, lard, marine oils, and mixtures thereof, which are fractionated, partially hydrogenated, and/or interesterified, are exemplary of the shortenings or fats which may be used in the present invention. Edible reduced- or low-calorie, or non-digestible fats, fat-substitutes, or synthetic fats, such as sucrose polyesters, which are process-compatible may also be used. Mixtures of hard and soft fats or shortenings and oils may be used to achieve a desired consistency or melting profile in the oleaginous composition. Exemplary of the edible triglycerides which can be used to obtain the oleaginous compositions for use in the present invention include naturally occurring triglycerides derived from vegetable sources such as soybean oil, palm kernel oil, palm oil, rapeseed oil, safflower oil, sesame oil, sunflower seed oil, and mixtures thereof. Marine and animal oils such as sardine oil, menhaden oil, babassu oil, lard, and tallow may also be used. Synthetic triglycerides, as well as natural triglycerides of fatty acids, may also be used to obtain the oleaginous composition. The fatty acids may have a chain length of from 8 to 24 carbon atoms. Solid or semi-solid shortenings or fats at room temperatures of, for example, from about 75° F. to about 95° F. may be used. Oleaginous compositions which may be used in the present invention may comprise purified soybean oil in which the lecithin has been removed during purification.

Medium chain triglycerides (MCTs) which may be employed for the encapsulation of calcium and enhancement of its absorption into the blood stream may preferably have a fatty acid chain length of six (6) to twelve (12) carbon atoms, most preferably eight (8) to ten (10) carbon atoms. Medium chain triglycerides may be synthesized from glycerol and fatty carboxylic acids. They also occur naturally in goat milk fat. Purified medium chain triglycerides may be a clear bland oil or solid at room temperature. They have a low caloric value, (e.g. 8.3 KCal/g), i.e. approximately 10% less than their longer chain counterparts (LCT). They also hydrolyze much more rapidly than LCT and exhibit a pronounced, positive effect on calcium absorption. The medium chain triglycerides may be synthesized from glycerin and fatty acids such as caproic, caprylic, capric, and lauric acids, and mixtures thereof. The preferred fatty acids are caprylic acid (octanoic acid, $C_8H_{16}O_2$) and capric (decanoic, $C_{10}H_{20}O_2$) acid. The relative amounts of the fatty acids may be varied to vary the melting point of the medium chain triglycerides. The medium chain triglycerides may have a melting point of from about room temperature to about 145° F.

Exemplary of a medium chain triglyceride which may be used is NEOBEE 1053 which is produced by Stepan Company, Northfield, Ill. It is a caprylic/capric triglyceride) made using glycerin from vegetable oil sources and medium-chain fatty acids from coconut or palm kernal oils. The fatty acid components of NEOBEE 1053 are $C_6$ (caproic acid) about 0.55% by weight, $C_8$ (caprylic acid) about 58.83% by weight, $C_{10}$ (capric acid) about 40.17% by weight, and $C_{12}$ (lauric acid) about 0.94% by weight. NEOBEE 1053 is a water white liquid with a hydroxyl value of about 5.0 and an iodine value of about 0.5.

The amount of shortening or fat, such as the medium chain triglycerides, may be used in plasticizing amounts which do not result in extruder surging or excessive oiliness in the encapsulated products. Exemplary amounts of the shortening or fat, such as the medium chain triglycerides, which may be employed in the present invention may be from about 4% by weight to about 15% by weight, based upon the weight of the glass-forming matrix materials such as mono- and di-glycerides, and oligosaccharides such as inulin. In embodiments of the invention, the shortening or fat content, or the MCT content of the encapsulated mineral and/or vitamin products may be from about 2.5% by weight to about 10% by weight, based upon the total weight of the encapsulated product.

In embodiments of the present invention water may optional be employed to help plasticize the dry ingredients such as the glass-forming matrix components such as the oligosaccharides and sugars, minerals, and vitamins, to reduce viscosity of the mixture, avoid excessive pressures, improve extrudability, and to avoid burning of the product. The optional water may be employed in amounts which do not adversely affect grindability and glassiness of the extruded composition, or which require excessive drying to obtain a non-rubbery grindable, consistency or glassy matrix. Taking into account all sources of water, such as optionally added water, and water inherently present in the one or more glass-forming matrix ingredients such as mono- and di-saccharides, inulin or other oligosaccharide ingredients, the total amount of water may range up to about 10% by weight, based upon the total weight of the glass-forming matrix ingredients such as mono-and di-glycerides, inulin, or other oligosaccharide ingredients. Generally, the glass-forming matrix materials, such as mono- and di-glycerides, and oligosaccharide ingredients such as RAFTILOSE 95, have a moisture content of up to about 5% by weight. Accordingly, additional water, for example up to about 5% by weight or more, may be added to provide a total moisture content of up to about 10% by weight, based upon the weight of the glass-forming matrix materials. In embodiments of the invention, upon exiting an extruder, some of the moisture flashes off, for example up to about 50% by weight of the water. The resulting water content of the extrudate may, for example, be less than about 5% by weight, preferably less than or equal to about 3% by weight, based upon the weight of the extrudate.

In accordance with the methods of the present invention, as schematically illustrated in FIG. 1, the one or more glass-forming matrix components, are preblended to form a dry mix, such as a sucrose/fructose sugar blend, or an oligofructose/lactose blend. The glass-forming matrix components are heated above their melting points or glass transition temperatures, or $T_g$ to form a molten mass or melt. In embodiments of the invention, the optional added water may be admixed with the glass-forming matrix components to form a mixture, and the mixture is heated to melt the glass-forming matrix components. The addition of the water tends to facilitate melting and plasticization of the glass-forming matrix components.

In embodiments of the invention oil may be admixed with the glass-forming matrix ingredients prior to melting. However, it is preferred that the oil be added after melting of the glass-forming matrix component. The oil tends to increase the glass transition temperature, $T_g$ thereby requiring more heat and making it more difficult to melt the glass-forming matrix component.

At least a substantial portion, or all of the encapsulant component, such as reduced iron, calcium, or other minerals and vitamins, such as ascorbic acid, is admixed with the oil component, such as fractionated milk fat, to form a pumpable oil-slurried encapsulant blend. The oil may be heated prior to or after addition of the encapsulant component to reduce viscosity of the slurry and to enhance pumpability. Also, use of a preheated slurry facilitates admixing with the molten glass-forming matrix components. The slurry may be heated to a temperature which is at least about 15° C. higher, for example about 30° C. to about 70° C. higher, than the melting point of the oleaginous composition. The resulting slurry is admixed with the molten glass-forming matrix components to form a substantially homogeneous molten blend.

In embodiments of the invention, any remaining portion of the encapsulant component may be dry blended with the glass-forming matrix components in the absence of the oil component to form a dry mix. Then, the mixture of glass-forming matrix components and the portion of the encapsulant component may be heated to melt the glass-forming matrix component in the presence of the encapsulant to form a molten mass or melt. The resulting melt may then be combined with the oil-slurried encapsulant to form a substantially homogeneous molten blend. The dry blending of a portion of the encapsulant component with the glass-forming matrix components permits the attainment of high encapsulant loading levels where inclusion of all of the encapsulant with the oil would deleteriously affect pumpability of the slurry or would require excessive amounts of oil to achieve pumpability.

The molten blend may then be cooled to obtain a formable, pliable, extrudable mass which is extruded through a die. The pliable extrudate is optionally cut into pieces, and optionally dried. The extrudate is cooled to form a solidified, grindable, non-rubbery glassy matrix containing an oil encapsulated mineral and/or vitamin encapsulant. The solidified, glassy extrudate may then be ground into a powder for incorporation into foods.

Generally, the melting temperature of the glass-forming matrix components such as the mono- and di-saccharides, and oligosaccharides having about 1% by weight to about 10% by weight moisture ranges from about 20° C. to about 200° C. The glass-forming matrix components, such as sucrose, fructose, lactose, maltodextrins, and inulin, are heated to above their melting point to allow for combining with the powdered or particulate encapsulant and with the slurry of oil and encapsulant. The glass-forming matrix components can be heated to temperatures substantially higher than their melting point to adjust viscosity of the melt provided it does not substantially destroy or inactivate the encapsulant or glass-forming matrix component, or result in discoloration. In embodiments of the invention, the glass-forming matrix components may be heated at least about 10° C., preferably at least about 15° C., for example about 25° C. to about 30° C. above their melting point or $T_g$.

In producing the slurry, the oleaginous component may be melted or heated and then admixed with the solid, particulate, or powdered encapsulant component to coat or encapsulate the encapsulant with the oleaginous component. The slurry is combined with the molten glass-forming matrix component which may optionally contain additional, non-oil-slurried encapsulant admixed therewith to form a molten mixture or magma.

In embodiments of the invention where non-slurried encapsulant is admixed with the glass-forming matrix materials, the admixing may be performed prior to or during heating or melting of the glass-forming matrix composition. In other variations, all or a portion of the materials can be separately heated and then combined to form the magma. Upon admixing with the slurry, any non-oil slurried encapsulant is coated or encapsulated by the oil of the slurry.

In embodiments of the present invention, the moisture content of the magma may be reduced to about 0.1% by weight to about 6% by weight, for example to about 1% by weight to about 3% by weight to remove supplemental moisture added as a processing aid. The moisture reduction may be achieved by maintaining the magma under pressures of at least 1 to 5 bar at a temperature of 95° C. to 175° C., reducing the pressure to 0.7 bar to 1.5 bar, preferably to atmospheric pressure, to flash off at least a portion of the moisture, and venting the moisture.

Thereafter, the magma is cooled, and may be subsequently formed into strands and further cooled to below the glass transition temperature to form an amorphous non-crystalline solid glassy matrix encapsulating the oil-coated encapsulant, such as reduced iron which is coated with fractionated milk fat. For formability into strands, the molten magma is cooled to form a plastic mass of sufficiently high viscosity so as to be able to be shaped into strands. In embodiments of the invention, the temperature of the magma may be reduced before forming from a hot temperature range of about 95° C. to about 200° C. to a temperature range of about 15° C. to about 125° C. After being formed into strands or ropes, the strands may be further cooled to a temperature of about 5° C. to about 40° C.

Thereafter, the cooled glassy matrix may be size reduced to form a powder having the requisite particle size. The particle size reduction may comprise cutting strands, ropes, or filaments of the glassy matrix. It may also involve crushing of matrix pieces to produce a crushed or granular mixture and then grinding the granular mixture to form a crushed and ground matrix pulverant or powdered matrix. In embodiments of the invention, the pulverant or powder may have a particle size as large as 1000 microns but preferably smaller than 800 microns and most preferably less than 500 microns but greater than 300 microns. If the particle size is reduced too much, the glassy matrix which encapsulates the particles of minerals may become too thin to prevent premature release of the encapsulant, or the encapsulant may be partially exposed. The encapsulant particles may, for example, have a largest dimension or diameter of about 35 microns. To avoid premature exposure of the encapsulant particles, the glassy matrix particles may have a particle size of at least about 50 microns, preferably at least 200 microns.

The glassy matrix of encapsulated minerals and/or vitamins so prepared may be employed as a mineral and/or vitamin fortification ingredient for a variety of food applications. The ingredient can be dry blended with other dry ingredients, or admixed with liquid ingredients for direct incorporation into foods or for topical application to foods.

Apparatus which may be employed to make the glassy matrix encapsulated minerals and/or vitamins may be a Fuisz machine such as is available from Fuisz Technologies, Ltd. (Chantily, Va.). A Fuisz machine can simplistically be compared to a cotton candy machine used to produce a glassy sugar floss confection. Another technology is to employ traditional boiled candy making apparatus and techniques to form the matrix pieces.

In embodiments of the invention, a melt comprising all ingredients may be made using conventional batch or continuous mixers. Subsequently, the melt may be fed into a single screw extruder which presses the melt through an extrusion die.

In other embodiments of the invention, the dough can be made continuously and using a continuous mixer or extruder alone. Twin screw extruders or co-rotating twin screw mixers may be advantageously used which enable the steps of continuously mixing the ingredients and subsequently extruding the glassy matrix through an extrusion die plate. In preferred embodiments, a twin screw extruder is used to practice the present invention. A twin screw extruder can perform the mixing, heating, optional moisture reduction, cooling and forming steps all in a single piece of equipment. As a result, a twin screw extruder provides the advantage of a practical and commercially economical technique for practicing the invention. It has been found desirable to use extruders which have at least two screws and that are capable of providing multiple zones with differing temperatures.

In other embodiments a twin screw extruder can be used to perform the mixing, heating and cooling steps while a second extruder, e.g., a single screw extruder, can be used to perform all but the mixing steps, for example, cooling and extruding in the form of filaments.

Co-rotating intermeshing twin screw extruders, such as those available from Buhler, Switzerland, Clextral France, Werner and Pfleiderer Germany, APV England or Wenger USA, or a Co-Kneader, available from Buss, Switzerland may be employed.

For feeding solid components to an extruder, conventional solids feeding devices such as a volumetric or gravimetric feeder may be used. Liquid injection nozzles may be used for injecting liquid active components or solutions, dispersions, emulsions, slurries or suspensions. In embodiments of the invention, a side feeder and liquid injection nozzles may be employed. If an injection nozzle is used, the pressure for injecting the liquid should be sufficiently higher than the pressure in the extruder so that the encapsulant can be injected into the extruder barrel. For example, if the pressure of the plasticized mass inside the extruder is 10 bars, the injection pressure may be about 2 to about 5 bars higher, i.e. 12 to 15 bars. In embodiments of the invention, ingredients such as the oil slurry may be injected or pumped into an open barrel of the extruder.

The admixing of the added active ingredients or encapsulants inside the extruder may be accomplished by using an appropriate extrusion screw configuration for achieving low shear mixing without substantially destroying the encapsulant or the glass-forming matrix components. Generally, the screw configuration in the barrels upstream of the slurry addition primarily functions to convey the ingredients for heating and melting. The screw configuration in the barrel where the slurry is added and in the barrels downstream thereof primarily functions to mix the ingredients. For example, a combination of alternating small pitch conveying elements with distributive mixing elements, that are staggered at an angle to each other for providing axially oriented leakage flow inside the extruder barrel may be employed. The combination of alternating conveying elements with distributive mixing elements cause the material flow to be continuously interrupted without shearing of the mass thus resulting in mixing of the material at low mechanical energy input.

An overall quantitative measure of the shear used inside an extruder, for example, is the specific mechanical energy input. In embodiments of the present invention, the specific mechanical input during admixing of the ingredients to obtain a formable mixture or dough may be below about 150 Wh/kg, preferably below about 100 Wh/kg, and most preferably below about 50 Wh/kg.

In embodiments of the invention, the pressure under which the formable mixture or dough may be formed may range from about 1 bar to about 150 bars, preferably from about 2 bars to about 100 bars. In embodiments of the invention, the mixture may be formed into individual shapes at pressures of about 5 bars to about 60 bars.

In other embodiments of the invention, other extruder screw configurations may be used that facilitate low shear distributive mixing, such as screw elements of the type ZME, TME, SME, and so-called IGEL elements commercially available from Werner and Pfleiderer. In embodiments of the invention, the length to diameter ratio (l/d) for the extruder may range up to about 50.

The total length of the distributive mixing section, for example, may be about 3 to 12 l/d to sufficiently admix and distribute and embed or encapsulate the added encapsulant or active components in the matrix.

The at least substantially homogeneous mixture of plasticized glass-forming matrix material, oil, and encapsulant may then be conveyed towards an extruder die plate. The conveying may be achieved by the use of low pitch extruder screw conveying elements which build up sufficient pressure prior to extruding the mix so that it can be forced through the apertures in the die plate. Another function of the low pitch elements is that they increase the degree of fill inside the last extruder barrel section. The increased degree of fill enables control of the temperature profile of the mix inside the extruder barrel for achieving optimum viscosity adjustment and extrusion through the subsequent die openings.

In other embodiments, screw configurations such as disclosed in U.S. Pat. No. 5,972,404 and International Patent Publication No. WO 98/18610 (published May 7, 1998) both to Bernhard van Lengerich, may be employed. The disclosures of U.S. Pat. No. 5,972,404 and International Patent Publication No. WO 98/18610 are herein incorporated by reference in their entireties.

The glassy matrix composition may be extruded through extrusion dies having aperture diameters of from about 0.10 mm to about 5 mm, generally less than about 1 mm, preferably from about 0.25 mm to about 1.0 mm. The diameter of the extrudate rope and product may be larger than the diameter of the die apertures due to deformation or swelling as the composition exits the die. The increase in diameter upon exiting the die may occur without substantial development of an expanded, puffed, foamy, or cellular structure. The extruded rope may have a cross-sectional diameter of from about 0.15 mm to about 5 mm, preferably from about 0.15 mm to about 4 mm, most preferably from about 0.25 mm to about 1.0 mm.

The extrudate rope may be cut at the die face using a rotating cutter, pelletizer, or rotating knives. In other embodiments, the extrudate rope may be cut away from the die using conventional cutting or forming means for producing pellets or tablets. The cut pieces, pellets, or tablets, may have a length:diameter ratio (l/d ratio) of about 0.5 to 10, preferably about 1.

In accordance with the process of the present invention, the particle size may be varied to control the surface to volume ratio of the pellets or pieces for achieving a desired controlled release of the encapsulant. The particle size may be varied, for example, by the use of different diameters for the extrusion die openings. Particle size may also be varied by the use of a variable speed cutter either at the die plate at the end of the extruder or away from the extruder after the ropes have been conveyed for a short distance. By varying the speed of the cutter, the size of the cut pieces may be varied for a given extruder throughput. The use of a variable cutter which is spaced a short distance from the die plate, for example, between about 0.5 meters to about 5 meters permits further surface cooling, further surface drying, and reduced stickiness to provide better cutting of the ropes into pellets.

After cutting, the resulting pieces or pellets may be dried to a sufficiently low moisture content which assures a sufficiently prolonged storage stability or shelf life. For example, the pellets may be dried to achieve a storage stability or shelf life of at least about six months, preferably at least about twelve months, most preferably at least about thirty-six months. In embodiments of the present invention, the drying may be performed using conventional drying equipment using drying temperatures which do not adversely affect the thermal stability of the encapsulants or matrix material. Exemplary drying temperatures may range from about 10° C. to about 50° C., for example from about 20° C. to about 30° C. The drying may be conducted to achieve a moisture content of less than about 5% by weight, preferably less than about 3% by weight. The product may be dried using a conventional fluidized bed or other conventional drying means.

Size reduction of the glassy filaments, strands, ropes, pellets, or pieces may be performed using conventional crushing and grinding equipment such as a hammer mill.

Figure 2:
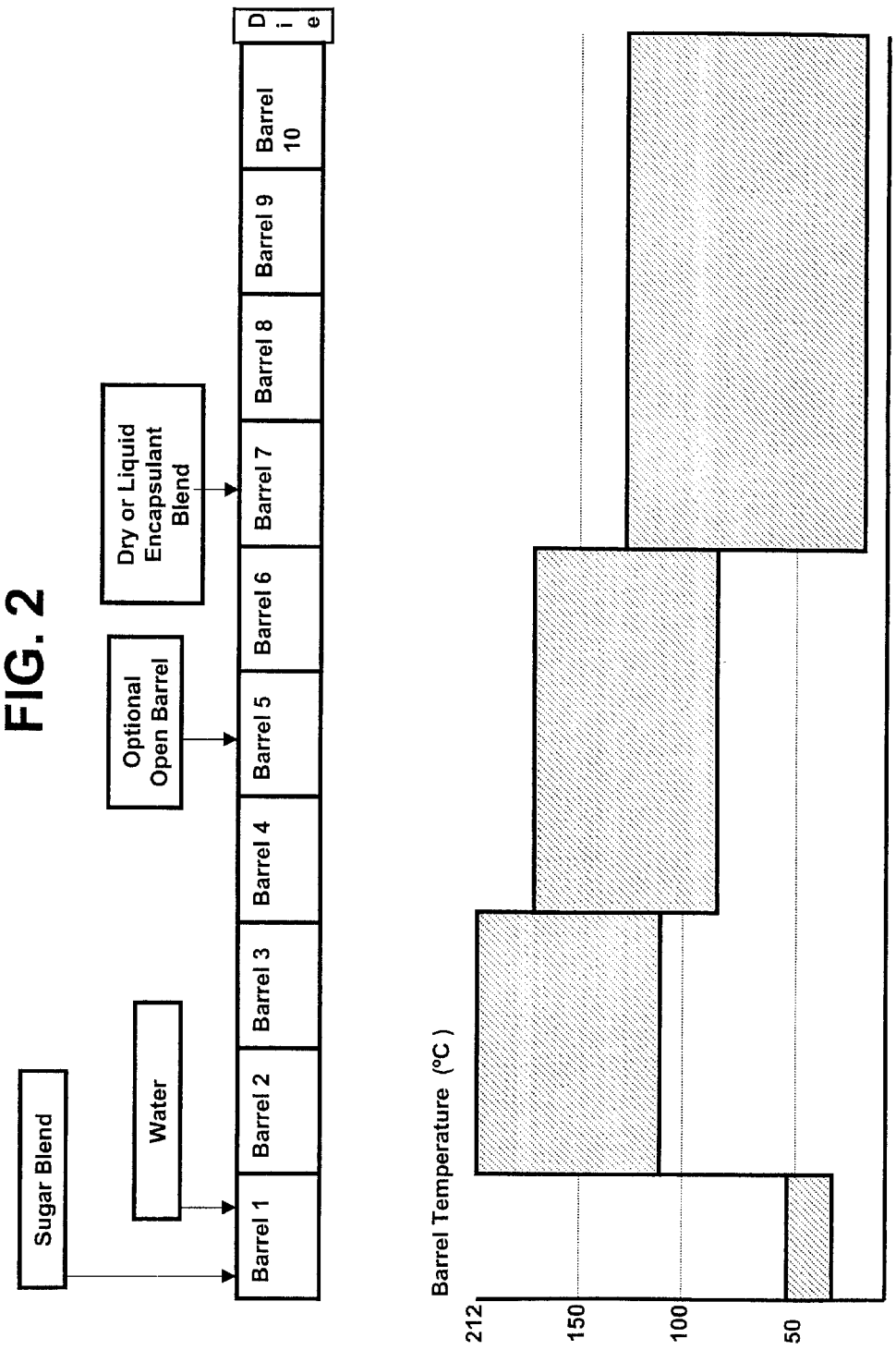
FIG. 2 is a schematic overview of the extrusion process of the present invention showing barrel set temperature profile ranges for the extruder for encapsulation of iron.

FIG. 2 shows schematically an overview of an extrusion process, an exemplary extruder barrel configuration, and exemplary set barrel temperatures or profiles in accordance with the present invention. The extruder may be a twin screw extruder having ten barrel sections. Barrels 1 through 6 may have screw configurations primarily for conveying of the ingredients. Barrels 7 through 10 may have screw configurations primarily for mixing of the ingredients. Each barrel may be individually externally heated or cooled in accordance with the barrel set temperatures. One or more glass-forming matrix materials such as a blend of sucrose and fructose may be prepared and stored or conditioned prior to feeding it into the extruder. The dry blend may be fed either gravimetrically or volumetrically into the feeding section of the extruder in barrel 1 through an open feed port. Optional water may also be fed into the open feed port of barrel 1. Temperatures at this barrel section are normally set at from about 30° C. to about 55° C. Simultaneously, the temperatures of barrel 2 and 3 may be set to about 110° C. to about 212° C. to rapidly heat and melt the sugar blend, that is conveyed into barrel 4. The barrel temperature in barrels 4, 5, and 6 may be set to about 80° C. to about 175° C. The temperature of the mix increases at a rate that is mainly affected by the contact time of the material and the barrel and exchange of material by the screws. The contact time is a function of rpm and throughput rate, which determine the degree of fill. The material exchange is affected by the screw configuration.

As long as the energy dissipation into the material is low, which is the case at a relative low material viscosity, the mass is heated via the barrel wall and its temperature is normally a few degrees lower than the actual barrel temperature. The blend forms a melt or magma, that may have a temperature of about 5° C. to 30° C. lower than the barrel temperature.

A vent opening may optionally be provided in barrel 5. The optionally open barrel section 5, optionally connected to a vacuum pump, allows the pressure to decrease substantially, for example from about 10 bar to about less than 1 bar. This pressure drop results in water evaporation and subsequent moisture loss of the molten mass. The amount of moisture evaporated to the atmosphere or to the vacuum, additionally depends upon the temperature of the product and residence time of the product in this open barrel section 5. Residence time is affected by the rpm of the screw, pitch of the screw elements, and available open area for water evaporation, which may vary from one, two or more vent ports. High barrel temperatures, above for example 150° C., force more steam to escape from the molten mass than low barrel temperatures, for example 125° C.

The subsequent barrels 7 through 10 may be cooled down with water to reduce mass temperature to achieve a formable mixture. Temperatures in these barrel sections may be set to about 15° C. to about 125° C. Barrel 7 may be open to the atmosphere to enable addition of a slurry of oil and encapsulant, such reduced iron and ascorbic acid. The temperature of the barrel may be adjusted depending upon the heat sensitivity of the encapsulant. However, generally minerals such as reduced iron and calcium carbonate are not heat sensitive and can withstand elevated temperatures without undergoing substantial destruction or inactivation. The product temperature at the encapsulant input location in barrel 7 is sufficiently low so as to not thermally destroy or disintegrate the encapsulant or glass-forming matrix component, but sufficiently high so as to facilitate mixing and encapsulation of the encapsulant in the molten glassy matrix material.

After the mix has been introduced into barrel section 7, it is conveyed into barrel section 8, then barrel section 9, and then barrel section 10, that mix the added ingredients into the matrix while preferably minimizing the introduction of shear energy. Simultaneously, the temperature of the barrels 8, 9, and 10 may be maintained low enough so as to not thermally destroy the encapsulant and to ensure that the viscous properties of the dough are sufficiently high to allow extrusion and forming of ropes, strands, or filaments that can be cut into pieces.

After exiting the barrel section 10 of the extruder, the mass enters into the die area, where it is distributed into a multitude of openings. The rate of extrudate per die area, may be less than about 5 kg/h per mm$^2$, preferably less than 3 kg/h per mm$^2$ and most preferably less than about 0.5 kg/h per mm$^2$. Excessively high rates will result in higher shear rates inside the die that can cause increased viscous dissipation, pressure and temperature which may adversely affect the encapsulant and may lead to unwanted product expansion.

In producing products for human or animal consumption, the particle size may be adjusted to achieving a controlled release of the encapsulant during passage of the pellets or particles through the mouth, the stomach, and the intestine. Variation of particle size also controls texture or mouthfeel and residence time of the pellets or particles inside the stomach. For example, particles smaller than 1 mm may have a less gritty mouthfeel and pass through the stomach or intestine faster than would particles larger than for example 2.5 mm.

The products of the present invention may possess a substantially non-chewable texture, which is perceived as being glassy o[00f8] fracturable, but is between the chewable texture of streusel or chewable vitamin pills, and the dense, hard glassy texture of uncooked pasta. The particles are generally uniform in size, glassy, powdery or granular to increase palatability to humans and animals, in a form that is easy to swallow with or without chewing. The products of the invention are generally at least substantially starch-free, non-expanded, not leavenable, and exhibit a non-puffed, substantially non-cellular, and glassy structure.

The encapsulated products of the present invention may be incorporated with or without grinding into foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain-based snacks, and microwave popcorn, dairy products such as yoghurt, cheese, and ice cream, sweet goods such as hard candy, soft candy, and chocolate, beverages, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food preblends or mixes for home or food service use, such as preblends for soups or gravy, dessert mixes, dinner mixes, baking mixes such as bread mixes, and cake mixes, and baking flour.

The encapsulated product may be redispersed as a liquid, or as a solid for human food, animal feed, or pharmaceutical purposes. The products of the present invention may be incorporated into foods for special purposes, such as performance foods, mood foods, medical foods, nutritional snacks or supplements, sport foods such as power bars, baby foods, toddler foods, infant foods, or foods for pharmaceutical purposes or other dietetic purposes. The discrete particulates or granules of the present invention may be used as a topping for breakfast cereals, snacks, soups, salad, cakes, cookies, crackers, puddings, desserts or ice cream. They may also be used as a granular ingredient for yogurts, desserts, puddings, custards, ice cream or other pasty or creamy foods.

The present invention is further illustrated by the following non-limiting examples where all parts, percentages, proportions, and ratios are by weight, and all temperatures are in ° C unless otherwise indicated:

EXAMPLE 1
Encapsulation of Iron in a Sugar Matrix

A 50 Kg mixture of fructose:sucrose (50:50 w/w) was prepared in a ribbon blender. The dry mix was placed in the hopper of a gravimetric feeder (K-Tron, Model KCL24T20) and further fed into the first barrel of a twin screw extruder (Buhler, DNDL-44) through the feed inlet at a rate of 12 Kg/hr. A Zenith® pump was used to pump water at a rate of 180 g/hr. The extruder consisted of 10-barrels with a screw diameter of 44 mm and a length to diameter ratio of 40. The extruder was divided into four temperature zones with specific barrel set temperatures as described in Table 1 below. Barrel configuration and temperature profile ranges which may be set are shown in FIG. 2.

TABLE 1

| Specific Barrel Temperature Profile | | | | | | | | | |
|---|---|---|---|---|---|---|---|---|---|
| Zone | 1 | 2 | 2 | 3 | 3 | 3 | 4 | 4 | 4 | 4 |
| barrel | 1 | 2 | 3 | 4 | 5 | 6 | 7 | 8 | 9 | 10 |
| Temp (° C.) | 50 | 205 | 205 | 165 | 165 | 165 | 100 | 100 | 100 | 100 |

The fructose-sucrose blend was melted as it traveled through the extruder's heated barrels. As the molten mass reached barrel 7, a blend of vitamin C/reduced iron/oil was fed into the extruder. The encapsulant blend consisted of 355 g ascorbic acid, finely ground (Roche, N.J.), 87 g reduced iron (American Chemical International) and 700 g fractionated milk fat, melting point (40° C.) obtained from Grassland Dairy Co (WI). The encapsulant blend was fed at a rate of 1.4 Kg/hr through a dedicated port using a peristaltic pump. Mixing of the encapsulant and the molten fructose-:sucrose blend commenced in barrels 7 through 10. The mass exited the extruder in the form of pliable opaque strands that were collected on trays and cooled for 30 minutes to 1 hr at ambient temperature to form a brittle glassy material. The cooled strands were further crushed in a Comil grinder (Quadro Engineering, Canada) that was equipped with an adequate mesh-size screen to obtain a particle size of the ground material, containing encapsulated iron, ranging from 300 μ to 500 μ.

Figure 3:
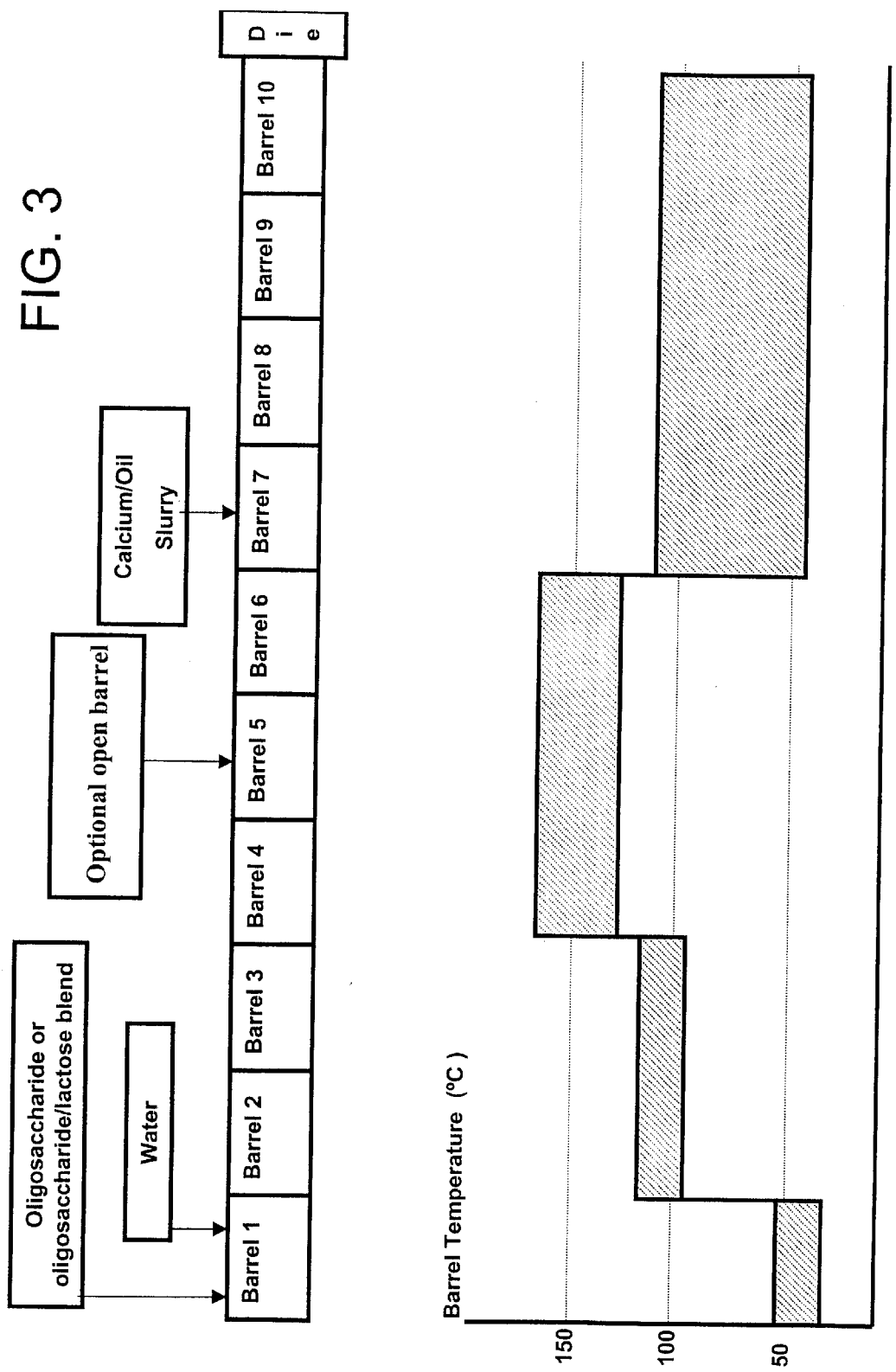
FIG. 3 is a schematic overview of the extrusion process of the present invention showing barrel set temperature profile ranges for the extruder for encapsulation of calcium.

EXAMPLE 2
Calcium Encapsulation in Fructoliaosaccharide/MCT:

50 Kg mixtures of fructooligosaccharide (brand name, RAFTILOSE 95 supplied by Orafti Co.) alone or blended with lactose were employed as a glass-forming dry mix matrix material. The dry mixing was performed in a ribbon blender. The weight ratios of RAFTILOSE 95 to lactose employed were 100:0, 95:5, and 90:10. The dry mix was placed in the hopper of a gravimetric feeder (K-Tron, Model KCL24T20) and further fed into the first barrel of a twin screw extruder (Buhler, DNDL-44) through the feed inlet at a rate of about 9 Kg/hr. A Zenith® pump was used to pump water at a rate of about 180 g/hr. The extruder consisted of 10-barrels with a screw diameter of 44 mm and a length to diameter ratio of 40. The extruder barrel was divided into four temperature zones. Barrel configuration and barrel set temperature profiles are shown in FIG. 3.

The RAFTILOSE or RAFTILOSE-lactose blend was melted as it traveled through the extruder's heated barrels. As the molten mass reached barrel 7, a slurry of calcium carbonate (OMYACAL FG-10) and a medium chain triglyceride (MCT)oil (NEOBEE 1053) was fed into the extruder through a dedicated port in barrel 7 at a rate of 4.5 Kg/hr using a Waukesha pump #2. The weight ratio of calcium carbonate:MCT was about 85:15. Mixing of the slurry and the molten RAFTILOSE or RAFTILOSE-lactose blend commenced in barrel 7 and continued through barrel 10. The mass exited the extruder in the form of pliable opaque strands that were collected on trays and cooled for about 30 min to about 1 hr at ambient temperature to form a brittle, glassy material. The cooled strands were further crushed in a Comil grinder (Quadro Engineering, Canada) that was equipped with an adequate mesh-size screen to obtain a particle size range from about 300 μ to about 500 μ. The product made with the RAFTILOSE-lactose 90:10 blend exhibited slight browning. No browning was exhibited with the RAFTILOSE-lactose 95:5 blend or the RAFTILOSE-lactose 100:0 sample.

EXAMPLE 3
Encapsulated Tri-Calcium Phosphate

Example 2 was repeated except that tricalcium phosphate (high density produced by Gadot) was used instead of the calcium carbonate in making the slurry.

EXAMPLE 4
Encapsulated Calcium Carbonate with Increased Calcium Load

Examples 2 and 3 were repeated except for the additional incorporation of dry calcium salt (carbonate or phosphate) with the RAFTILOSE or RAFTILOSE-lactose blend. This approach was used to increase the calcium load in the encapsulating matrix. In such mixes, concentrations of elemental calcium [$Ca^{+2}$] in the dry feed were kept at about 15% by weight, based upon the dry weight of the RAFTILOSE or RAFTILOSE-lactose. Addition of higher levels of calcium salts tended to result in browning of the RAFTILOSE and the development of objectionable flavor.

What is claimed is:

1. A method for encapsulating a mineral or vitamin in a glassy matrix comprising:
   a. admixing an encapsulant component comprising at least one mineral or vitamin with an edible oil to obtain a slurry wherein said at least one mineral or vitamin is encapsulated by said oil,
   b. admixing said slurry with a melt comprising at least one molten glass-forming matrix material to obtain a molten blend, and
   c. cooling the molten blend to encapsulate the oil encapsulated mineral or vitamin in a glassy matrix.

2. A method as claimed in claim 1 wherein said molten blend is cooled to obtain a formable, pliable mass, and the formable, pliable mass is formed into pieces.

3. A method for the fortification of a food with a mineral or vitamin comprising incorporating the pieces obtained in claim 2 into the food wherein the pieces are cut pieces, pellets or tablets having a length:diameter (l/d) ratio of from about 0.5 to about 10.

4. A method as claimed in claim 3 wherein said l/d ratio is about 1.0.

5. A method as claimed in claim 2 wherein the formable, pliable mass is extruded through a die into ropes, strands or filaments which are cut into said pieces, and the pieces are cooled to obtain said glassy matrix.

6. A method as claimed in claim 2 wherein the formable, pliable mass is cut into pieces, and the pieces are ground.

7. A method as claimed in claim 1 wherein additional encapsulant component is admixed with said glass-forming matrix material, and the glass-forming matrix material is heated in the presence of said additional encapsulant component to form said melt.

8. A method as claimed in claim 1 wherein water is admixed with said glass-forming matrix material, and the glass-forming matrix material is heated in the presence of the water to form said melt.

9. A method as claimed in claim 7 wherein water is admixed with said glass-forming matrix material, and the glass-forming matrix material is heated in the presence of the water and the additional encapsulant component to form said melt.

10. A method as claimed in claim 1 wherein said glass-forming matrix material comprises at least one mono- or di-saccharide.

11. A method as claimed in claim 1 wherein additional encapsulant component, at least one mono- or di-saccharide, and at least one oligosaccharide are dry blended and heated to obtain said melt.

12. A method as claimed in claim 1 wherein said encapsulant component comprises at least one mineral selected from the group consisting of iron, magnesium, copper, zinc and selenium.

13. A method as claimed in claim 1 wherein said at least one glass-forming matrix material comprises sucrose and fructose.

14. A method as claimed in claim 1 wherein said encapsulant component comprises an iron salt, and the amount of iron is sufficient to provide an elemental iron content of about 0.5% by weight to about 10% by weight, based upon the weight of said at least one glass-forming matrix ingredient.

15. A method as claimed in claim 14 wherein said at least one glass-forming matrix ingredient comprises sucrose and fructose.

16. A method as claimed in claim 15 wherein said edible oil comprises a saturated fat.

17. A method for fortification of a food with a mineral or vitamin comprising incorporating a powdered glassy matrix obtained by the method of claim 1 into the food.

18. A method for encapsulating a mineral component in a glassy matrix comprising:
a. admixing a mineral component with an edible oil to obtain a slurry wherein said mineral component is encapsulated by said oil,
b. admixing said slurry with a melt comprising at least one molten glass-forming matrix material to obtain a molten blend, and
c. cooling the molten blend to obtain a formable, pliable mass,
d. extruding the formable, pliable mass to obtain an extrudate, and
e. cooling the extrudate to obtain a glassy matrix.

19. A method as claimed in claim 18 wherein the extrudate is formed into pieces by cutting.

20. A method as claimed in claim 19 wherein the cut pieces are ground into a powder.

21. A method as claimed in claim 18 wherein additional mineral component is admixed with said glass-forming matrix material, and the glass-forming matrix material is heated in the presence of said additional mineral component to form said melt.

22. A method as claimed in claim 18 wherein water is admixed with said glass-forming matrix material, and the glass-forming matrix material is heated in the presence of the water to form said melt.

23. A method as claimed in claim 22 wherein said glass-forming matrix material comprises at least one sugar selected from the group consisting of sucrose, fructose and lactose, said oil comprises a saturated fat, and said mineral component comprises at least one mineral selected from the group consisting of iron, magnesium, copper, zinc and selenium.

24. A product obtained by the method of claim 18.

25. A product as claimed in claim 24 which is in the form of cut pieces, pellets or tablets having a length: diameter (l/d) ratio of from about 0.5 to about 10.

26. A product as claimed in claim 25 wherein said l/d ratio is about 1.0.

27. A mineral fortified food product containing a product obtained by the method of claim 18.

28. A mineral fortified food product as claimed in claim 27 which is a ready-to-eat cereal.

29. A mineral fortified food product as claimed in claim 27 which is a yogurt.

30. An ingredient for fortification of a food product with a mineral which ingredient comprises cut pieces, pellets or tablets comprising a glassy matrix encapsulating an oil-encapsulated mineral component, wherein said glassy matrix comprises at least one mono- or di-saccharide.

31. An ingredient as claimed in claim 30 wherein said glass-forming matrix material comprises sucrose, fructose, lactose, or mixtures thereof.

32. A mineral fortified food product comprising an ingredient as claimed in claim 31.

33. A mineral fortified food product as claimed in claim 32 which is a ready-to eat cereal or yogurt.

34. An ingredient as claimed in claim 30 wherein the mineral is a mixture of calcium and at least one member selected from the group consisting of iron, magnesium, copper, zinc and selenium, the elemental calcium content of said ingredient being at least about 10% by weight, based upon the total weight of said at least one mono- or di-saccharide.

35. An ingredient as claimed in claim 34 wherein said elemental calcium content of said ingredient is about 15% by weight to about 32% by weight, based upon the total weight of said at least one mono- or di-saccharide.

36. An ingredient as claimed in claim 30 which is a powder having a particle size of about 200 microns to about 800 microns.

37. A mineral fortified food product comprising an ingredient as claimed in claim 30.

38. A mineral fortified food product as claimed in claim 37 which is a ready-to eat cereal or yogurt.

39. An ingredient as claimed in claim 30 wherein the ingredient comprises cut pieces which are uniform in size.

40. An ingredient as claimed in claim 30 wherein said glassy matrix comprises a mixture of lactose with sucrose or fructose, and further wherein the weight ratio of lactose to the total amount sucrose or fructose ranges from about 5:95 to about 50:50.

41. An ingredient as claimed in claim 30 wherein said glassy matrix enhances absorption of calcium into the bloodstream.

42. An ingredient as claimed in claim 30 wherein the oil in said oil-encapsulated mineral component comprises a medium chain triglyceride to enhance the absorption of calcium into the bloodstream or a fractionated milk fat.

43. An ingredient as claimed in claim 42 wherein the amount of said medium chain triglyceride is from about 2.5% by weight to about 10% by weight, based on the total weight of the ingredient.

44. An ingredient as claimed in claim 30 wherein said cut pieces, pellets or tablets have a length:diameter (l/d) ratio of from about 0.5 to about 10.

45. An ingredient as claimed in claim 44 wherein said l/d ratio is about 1.0.

* * * * *